(12) United States Patent
Gran et al.

(10) Patent No.: US 11,751,849 B2
(45) Date of Patent: Sep. 12, 2023

(54) HIGH-RESOLUTION AND/OR HIGH-CONTRAST 3-D AND/OR 4-D ULTRASOUND IMAGING WITH A 1-D TRANSDUCER ARRAY

(71) Applicant: B-K Medical Aps, Herlev (DK)

(72) Inventors: Fredrik Gran, Limhamn (SE); Svetoslav Ivanov Nikolov, Farum (DK); Jens Munk Hansen, Kobenhavn N (DK); Robert Harold Owen, Stenlose (DK)

(73) Assignee: B-K Medical Aps, Herlev (DK)

( * ) Notice: Subject to any disclaimer, the term of this patent is extended or adjusted under 35 U.S.C. 154(b) by 855 days.

(21) Appl. No.: 15/716,626

(22) Filed: Sep. 27, 2017

(65) Prior Publication Data

US 2019/0090850 A1   Mar. 28, 2019

(51) Int. Cl.
*A61B 8/00* (2006.01)
*A61B 8/12* (2006.01)
*A61B 8/08* (2006.01)

(52) U.S. Cl.
CPC ............ *A61B 8/467* (2013.01); *A61B 8/12* (2013.01); *A61B 8/445* (2013.01); *A61B 8/4444* (2013.01); *A61B 8/4461* (2013.01); *A61B 8/5207* (2013.01); *A61B 8/4254* (2013.01); *A61B 8/466* (2013.01)

(58) Field of Classification Search
CPC ......... A61B 8/467; A61B 8/5207; A61B 8/12; A61B 8/445; A61B 8/4444; A61B 8/4461; A61B 8/466; A61B 8/4254; G01S 7/5209; G01S 7/52095
See application file for complete search history.

(56) References Cited

U.S. PATENT DOCUMENTS

| 6,139,501 A * | 10/2000 | Roundhill ............... A61B 8/06 600/443 |
| 6,231,511 B1 | 5/2001 | Bae |
| 9,289,187 B2 | 3/2016 | Owen et al. |

(Continued)

FOREIGN PATENT DOCUMENTS

WO    2017149352 A1    9/2017

OTHER PUBLICATIONS

Andresen, et al., Synthetic Aperture Focusing for a Single-Element Transducer Undergoing Helical Motion, IEEE vol. 58, No. 5, May 2011.

(Continued)

*Primary Examiner* — Serkan Akar
*Assistant Examiner* — Amal Aly Farag
(74) *Attorney, Agent, or Firm* — Daugherty & Del Zoppo, Co. LPA

(57) ABSTRACT

An ultrasound imaging system includes a probe and a console. The probe includes an elongate shaft with a long axis, a transducer array disposed the shaft along the long axis and configured to generate signals indicative of received echoes, and a motor with a position sensor configured to rotate the shaft within a predetermined arc. The console includes a beamformer configured to process the signals from the transducer array and generate at least a volume of data for each sweep of the transducer array along the arc. The console further includes a display configured to display the volume of data.

23 Claims, 7 Drawing Sheets

(56) References Cited

U.S. PATENT DOCUMENTS

| | | | |
|---|---|---|---|
| 2005/0085730 A1* | 4/2005 | Flesch | A61B 8/12 600/459 |
| 2009/0067699 A1* | 3/2009 | Clark | A61B 8/463 382/131 |
| 2009/0069692 A1* | 3/2009 | Cooley | G01S 7/52028 600/459 |
| 2009/0182235 A1* | 7/2009 | Robert | G01S 7/52028 600/443 |
| 2010/0152590 A1* | 6/2010 | Moore | A61B 8/4461 600/466 |
| 2010/0156404 A1* | 6/2010 | Han | A61B 8/12 324/251 |
| 2013/0261466 A1* | 10/2013 | Owen | A61B 8/12 600/463 |
| 2016/0338676 A1* | 11/2016 | Berger | G16H 20/40 |
| 2018/0168544 A1* | 6/2018 | Davidsen | A61B 8/403 |

OTHER PUBLICATIONS

Frazier, C., et al., Synthetic Aperture Techniques with a Virtual Source Element, IEEE vol. 45, No. 1, Jan. 1998.

Freeman, et al., Retrospective Dynamic Transmit Focusing, Ultrasonics Imaging 17, 173-196, 1995.

Jensen, Gori, Spatial filters for focusing ultrasound images, 2001 IEEE Ultrasonics Symposium Proceedings, 2001.

Jespersen, et al., Multi-Angle Compound Imaging, Ultrasonic Imaging 20, 81-102, 1998.

Kasai, et al., Real-Time Two-Dimensional Blood Flow Imaging Using an Autocorrelation Technique, IEEE vol. Su-32, No. 3, May 1985.

Laakso, et al., Splitting the Unit Delay—Tools for fractional delay filter design, IEEE Signal Processing Magazine, Jan. 1996.

Lockwood, et al., Real-Time 3-D Ultrasound Imaging Using Sparse Synthetic Aperture Beamforming, IEEE vol. 45, No. 4, Jul. 1998.

Nikolov and Jensen, 3D synthetic aperture imaging using a virtual source element in the elevation plane, IEEE Ultrasonics Symposium, 2000.

Nikolov and Jensen, Velocity estimation using synthetic aperture imaging, IEEE Ultrasonics Symposium 2001.

Nikolov, et al., Practical Applications of Synthetic Aperture Imaging, IEEE Ultrasonics Symposium, Oct. 2010.

Nikolov, et al., Synthetic Aperture Imaging Using a semi-analytic model for the transmit beams, IEEE Ultrasonics Symposium, Oct. 2015.

Hansen, et al., Spatial Delay Beamformation, U.S. Appl. No. 15/388,259, filed Dec. 22, 2016.

Andresen, et al., Synthetic Aperture Focusing for a Single Element Transducer undergoing Helix Motion, IEEE Transactions on Ultrasonics, Ferroelectrics and Frequency Control, 2011.

Nikolov and Jensen, 3D Synthetic Aperture imaging using a virtual source element in the elevation plane, IEEE Ultrasonics Symposium, Oct. 2000.

* cited by examiner

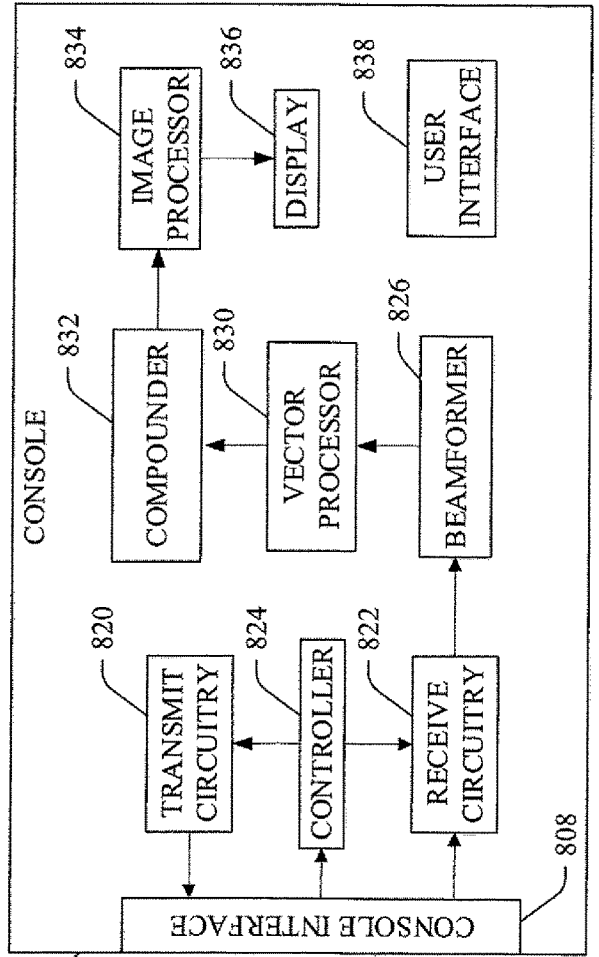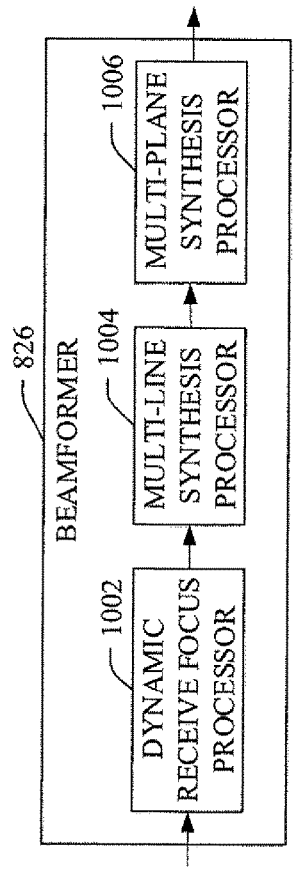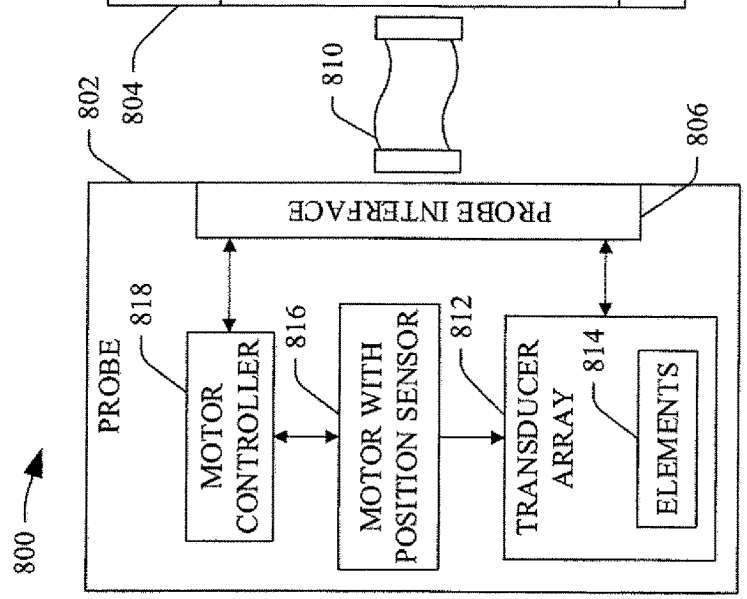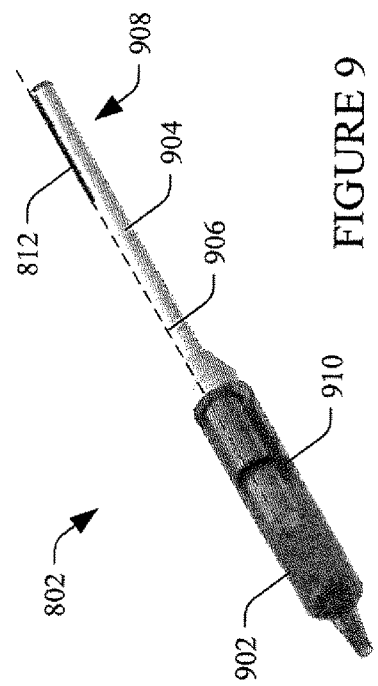
FIGURE 8
FIGURE 9
FIGURE 10

HIGH-RESOLUTION AND/OR HIGH-CONTRAST 3-D AND/OR 4-D ULTRASOUND IMAGING WITH A 1-D TRANSDUCER ARRAY

TECHNICAL FIELD

The following generally relates to ultrasound (US) imaging and more particularly to high-resolution and high-contrast 3-D and/or 4-D ultrasound imaging with a one-dimensional (1-D) transducer array.

BACKGROUND

Ultrasound (US) imaging has provided useful information about the interior characteristics of a subject under examination. A general US system includes a probe with a transducer array of a plurality of transducer elements and a console for controlling the array of transducers for transmitting ultrasonic waves and receiving echoes, which are processed to generate images of the interior characteristics of the subject under examination, including three-dimensional (3-D) volumes and/or four-dimensional (4-D) data sets.

Probes intended for trans-rectal and trans-vaginal use are designed for particular applications. Such probes have included an elongate cylindrical-shaped shaft with the transducer array affixed at or near an end region of an end of the shaft configured to insert into the rectal or vaginal cavity and the other end connects to a handle of the probe. Such probes have included a multi-element (linear and curved) transducer array arranged along a long axis of the shaft that emit pressure waves in a direction generally parallel to the axis and perpendicular to the shaft.

The transducer array has been configured to rotate through a plurality of predetermined angles within a predetermined arc. By rotating the transducer and actuating a set of elements at each angle, a plurality of 2-D scans is performed, resulting in a plurality of 2-D image/scanplanes which collectively form a 3-D volume. FIG. 1 shows an example probe 100 with a transducer array 102, FIG. 2 shows the probe 100 and one 2-D scanplane 202, and FIG. 3 shows a portion of the probe 100 and a 3-D volume 302, which includes a plurality of the 2-D scanplanes 202, each for a different scan angle.

The scanplanes 202 are shown in FIGS. 2 and 3 as "paper" thin sheets for illustrative purposes. The "natural" coordinate system for the acquisition is cylindrical-rotational angle, lateral position and depth. For image display, the scanplanes 202 have been considered as planes with uniform thickness when the data is mapped from the cylindrical coordinate system to the Cartesian coordinate system. FIG. 4 shows an example in which the scanplane 202 is modeled as having a uniform thickness 402 and uniform width 404.

For 3-D and/or 4-D images, the console creates transverse planes, which are orthogonal to the imaging scanplanes 202. FIG. 5 shows an example of one transverse plane 502, which is orthogonal to the scanplane 202 and the transducer array 102. The volume reconstruction presumes uniform width (in the scanplane) and thickness (in the transverse plane), as shown in FIG. 4. The use of dynamic receive focusing in combination with retrospective transmit focusing, plane wave compounding, and synthetic transmit focusing produces beams that have uniform width in the imaging plane. However, the beam has a varying thickness in the transverse plane.

This is illustrated in FIG. 6. In FIG. 6, a transverse plane 602 has an initial thickness close to the array 102 and converges around an elevation focus 602 of the array 102 in a near field 604 resulting in a narrower thickness, and then diverges to a greater thickness in a far field 606. The greater thickness results in lower resolution and contrast in these regions. Unfortunately, this renders this approach less than optimal for examinations which could benefit from high spatial resolution close to the array such as trans-rectal and trans-vaginal 3-D imaging. FIG. 7 shows an example a 3-D image generated using data acquired as discussed in connection with FIGS. 1-6.

SUMMARY

Aspects of the application address the above matters, and others.

In one aspect, an ultrasound imaging system includes a probe and a console. The probe includes an elongate shaft with a long axis, a transducer array disposed on or within the shaft along the long axis and configured to generate signals indicative of received echoes, and a motor with a position sensor configured to rotate the shaft within a predetermined arc. The console includes a beamformer configured to process the signals from the transducer array and generate at least a volume of data for each sweep of the transducer array along the arc. The console further includes a display configured to display the volume of data.

In another aspect, a method includes receiving signals from a probe, which includes an elongate shaft with a long axis, a transducer array disposed on or within the shaft along the long axis and configured to generate the signals indicative of received echoes, and a motor with a position sensor configured to rotate the shaft within a predetermined arc. The method further includes beamforming the signals to generate at least a volume of data for each sweep of the transducer array along the arc. The method further includes displaying the volume of data.

In another aspect, a computer readable medium is encoded with computer executable instructions which when executed by a processor causes the processor to: receive signals from a probe, which includes an elongate shaft with a long axis, a transducer array disposed on or within the shaft along the long axis and configured to generate the signals indicative of received echoes, and a motor with a position sensor configured to rotate the shaft within a predetermined arc, beamform the signals to generate at least a volume of data for each sweep of the transducer array along the arc, and visually present the volume of data.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIG. 8 schematically illustrates an example ultrasound imaging system with a probe and a console with beamformer configured to generate GOOD IMAGES.

FIG. 9 schematically illustrates an example of the probe of FIG. 8.

FIG. 10 schematically illustrates an example beamformer including a dynamic receive focus processor, a multi-line synthesis processor, and a multi-plane synthesis processor.

DETAILED DESCRIPTION

Figure 1:
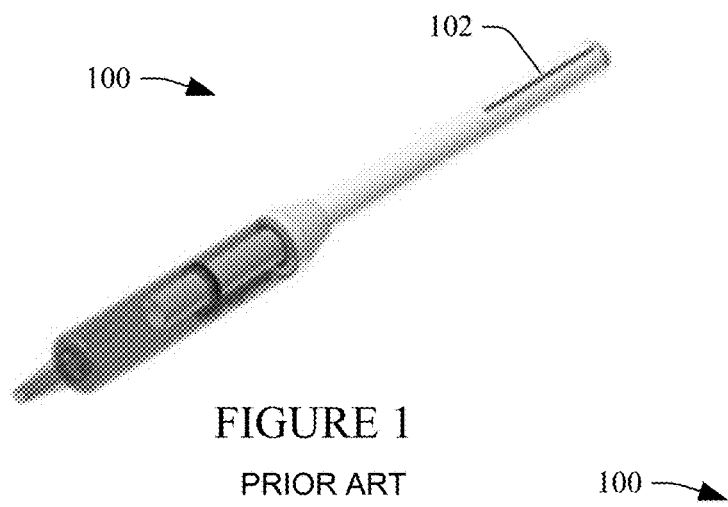
FIG. 1 show a prior art probe with a linear 1-D transducer array.
Figure 2:
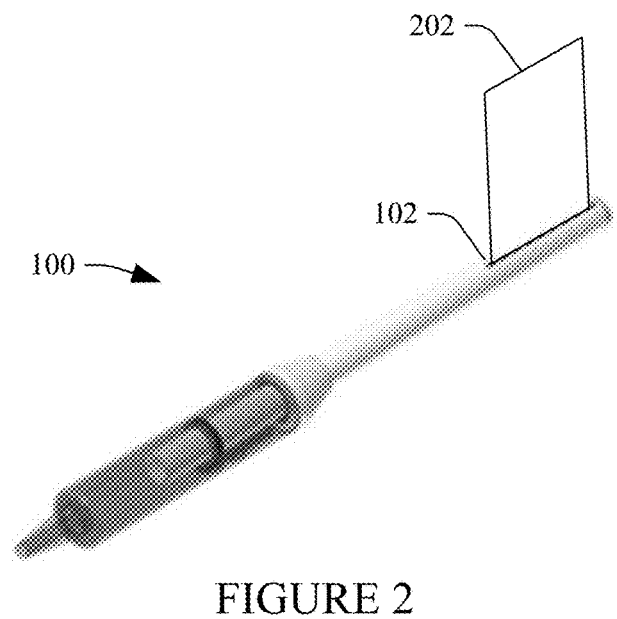
FIG. 2 shows the prior art probe and a corresponding image plane.
Figure 3:
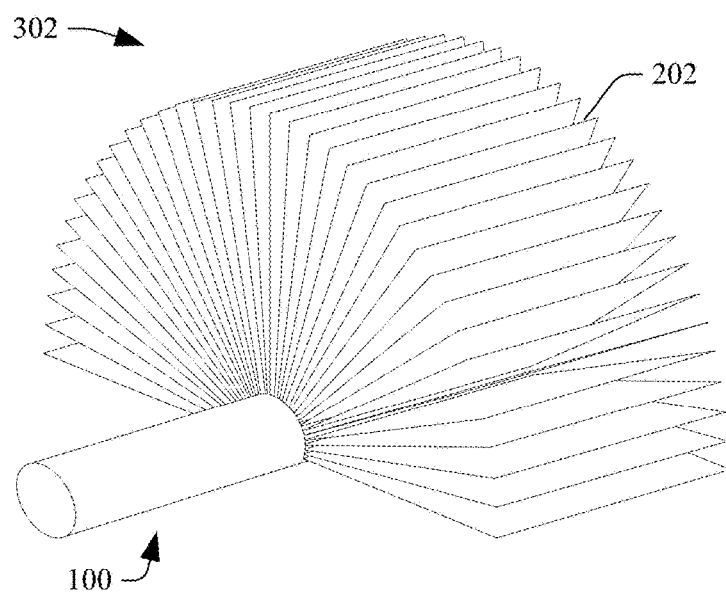
FIG. 3 shows the prior art probe with a plurality of image planes, each for a different scan angle.
Figure 4:
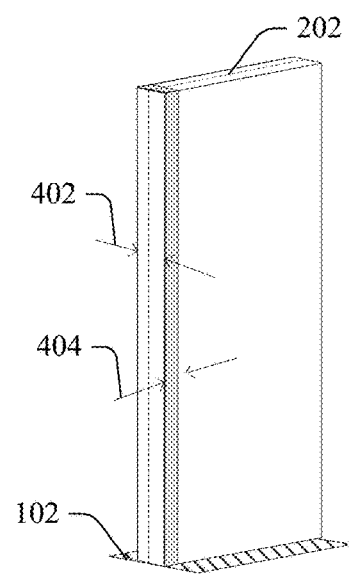
FIG. 4 shows an example in which the image plane of the FIG. 3 is modeled as having a uniform thickness and uniform width.
Figure 5:
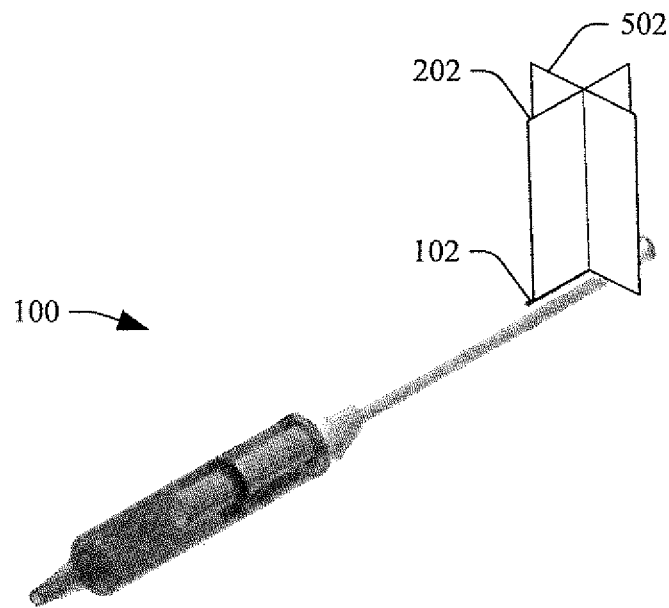
FIG. 5 shows the prior art probe with image plane and a transverse plane.
Figure 6:
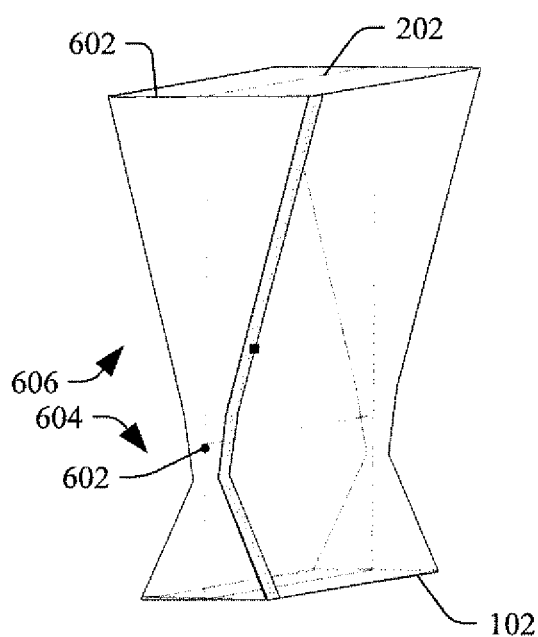
FIG. 6 shows an actual image plane of the prior art probe with varying thickness in the transverse direction.
Figure 7:
FIG. 7 shows an example a 3-D image generated with the probe of FIG. 1.

FIG. 8 illustrates an imaging system 800, such as ultrasonic imaging system, including an ultrasound (US) transducer probe 802 and a console 804. The imaging system 800 is configured for high-resolution and high-contrast 3-D and/or 4-D imaging.

The probe 802 includes a probe interface 812 with input and output ports for communicating signals with the console 804. The console 804 includes a console interface 808 with input and output ports for communicating signals with the probe 802. The probe interface 806 and the console interface 808 communicate with each other through a communication path 810 such as a hardware channel (e.g., a cable) and/or a wireless channel.

The probe 802 includes a transducer array 812 with a plurality of transducer elements 814 arranged along a long axis of the array. In this embodiment, the transducer array 812 ray includes a one dimensional (1-D) linear or curved array with 16, 64, 128, 196, 256, etc. transducer elements 814. In other embodiments, the transducer array 812 includes a different number of transducer elements and/or a two-dimensional (2-D) array of the transducer elements 814.

The transducer elements 814 are configured to emit an ultrasound signal (e.g., focused beams, plane waves, or diverging waves) in response to excitation signals from the console 804. The transducer elements 814 are also configured to receive echo signal, generate electrical (RF) signals indicate thereof, and transmit the electrical signals to the console 804 over the communication path 810. In general, an echo signal is generated in response to the ultrasound signal interacting with structure such as anatomical tissue, organs, cells, etc.

In the illustrated embodiment, the transducer array 812 is configured for autonomous movement to rotate within a predetermined arc in a plane orthogonal to (e.g., a transverse plane) the long axis or image plane (e.g., wobbles around the long axis). In one instance, the arc is one hundred and eighty degrees (180°). In another embodiment, the arc is less or greater than 180°. An example of a probe configured for such rotation is described in U.S. Pat. No. 9,289,187 B2, filed Dec. 10, 2010, and entitled "Imaging transducer probe," which is incorporated by reference in its entirety herein.

A motor 816 is configured to rotate the transducer array 812 and includes a position sensor configured track the rotational position and/or rotation speed of the transducer array 812. A motor controller 818 controls the motor 816 based on parameters such start and stop angular positions, speed of rotation, direction of rotation, a number of synchronization pulses between the start and stop positions, etc. The motor controller 818 receives parameters from the console 804 and transmits tracked rotational position and/or rotation speed to the console 804.

The illustrated probe 802 is an endocavitary probe such as a trans-rectal and/or trans-vaginal probe configured for insertion into and imaging within cavities such as the rectum, vagina, and/or other cavity. FIG. 9 schematically illustrates an example of such a probe. In this example, the probe 802 includes a handle portion 902, a generally cylindrical elongate shaft 904 extending therefrom, and the transducer array 812 is arranged along a long axis 906 near an end region 908 of the shaft 904. The handle 902 is shown semi-transparent and houses a drive system 910, which rotates the shaft 904. An example of such a probe is the 9038 of BK Ultrasound, headquartered in MA, USA.

Returning to FIG. 8, the console 804 includes a transmit circuit 820 that transmits over the communication path 810 a signal that selectively excites one or more of the elements 814 to emit pressure waves, and a receive circuit 822 that receives the electrical signal generated by the elements 814 over the communication path 810. The receive circuit 822 may also be configured to process the electrical signal, including, amplify the signal, convert the signal to a digital signal, etc.

A controller 824 controls the transmit circuitry 820 to control one or more of the elements 814 to transmit, steer, focus, etc. for an A-mode, B-mode, C-plane, etc. acquisition. The controller 824 also controls the receive circuitry 822, e.g., to steer and/or focus the received signals. The controller 824 receives, over the communication path 810, trigger signals from the probe 802 at pre-defined time intervals, transducer position and motion direction signals and synchronizes operation of the transmit and the circuitry 820 and 822 and processing of the received electrical signals.

A beamformer 826 processes the signals and produces a high-quality image. As described in greater detail below, this includes performing dynamic receive beamforming, combining the results thereof and applying delays that depend on a transmit wave-form and synthesizing multiple lines dynamically focused in the imaging plane, and beamforming the synthesized lines in a plane along a direction of rotation to produce the high-quality 3-D image. In one instance, this beamforming, along with subsequent processing of the data, improves a resolution and a contrast of an image close to a surface of the transducer array 102 and in the far field.

A vector processor 830 is configured to perform B-mode processing such as depth-dependent band-pass filtering, gain adjustment, envelope detection and decimation, on each individual line. A compounder 832 is configured to perform non-coherent compounding on the envelope detected data (without phase information). In one instance, the compounding reduces speckle and/or enhances edges. An image processor 834 is configured to filter and enhance the data. A display 836 is configured to display the data. A user interface 828 includes various input and/or output devices such as buttons, a touch screen, etc. and allows a user to interact with the imaging system 800.

The beamformer 826, the vector processor 830, the compounder 832, and/or the image processor 834 can be implemented via a hardware processor (e.g., a central processing unit (CPU), a microprocessor, etc.) executing computer readable instructions embedded and/or encoded on computer readable medium (which excludes transitory medium) such as a memory device and/or other non-transitory medium. The processor can also computer readable instructions carried by transitory medium such as a signal, a carrier wave, and/or other transitory medium.

In general, the approach described herein may improve diagnosis and/or treatment planning, which may improve patient outcomes and quality of life. For example, transrectal imaging of the anal sphincter and proximal rectal wall may benefit with better imaging of the various layers and types of muscle involved in this complex anatomy. Enhanced visualization of any pathology will facilitate with diagnosis and possible treatment planning. Trans-rectal imaging of the prostate with enhanced resolution may allow improved location and identification of abnormalities and possible cancerous lesions. Trans-vaginal imaging of the pelvic floor with enhanced resolution may improve the ability to view muscle motion, segment the various muscle layers, view the bladder neck and associated muscle groups, etc.

FIG. 10 schematically illustrates an example of the beamformer 826.

A dynamic receive focus (DRF) processor 1002 receives, as input, the signal from the receive circuitry 822 (FIG. 8). The dynamic receive focus processor 1002 is configured to add a header to each received signal. In one instance, a part of each header contains the angle of the transducer array 812 at which the data for the beam was acquired. As described in greater detail below, the dynamic receive focus processor 1002 produces, via delay and sum beamforming, a set lines in the imaging plane for every transmission.

A multi-line synthesis (MLS) processor 1004 is configured to apply delays and weights on lines which have a same origin and direction, but are acquired with different transmissions. This process corresponds to coherent plane wave compounding when the transmissions are planar waves sent at different angles, synthetic aperture focusing when the transmit waves are defocused, or retrospective transmit beamforming when the transmission is focused.

A multi-plane synthesis (MPS) processor 1006 is configured to apply delays and weights on lines acquired from different imaging planes, but which have a same origin and direction relative to the array at a given angular position. The weights and delays are calculated in accordance to a shape of the beam in the transverse plane. The output is X 3-D volumes of RF data for each sweep of the transducer array 812. In one instance, X is a value such as 1, 2, 3, 4, 5, . . . . Each of the volumes correspond to RF lines that have been acquired using different (receive) apertures to beamform the same point in the imaging plane, and/or different transmit directions.

In one instance, the beamformer 826 of FIG. 10 can be considered a three-stage beamformer, with the dynamic receive focus processor 1002 the first stage, the multi-line synthesis processor 1004 the second stage, and the multi-plane synthesis processor 1006 the third. The beamformer 826 can include all three stages (as shown) or at least two of the stages are implemented via different beamformers. For example, each of the processor 1002, 1004 and 1006 could be implemented by a different beamformer.

The following describes non-limiting examples of the dynamic receive focus processor 1002, the multi-line synthesis processor 1004 and the multi-plane synthesis processor 1006. For these examples, for a given angular position ($\theta_j$) of the transducer array 812, the console 804 produces N RF-images, where N is the number of images used to achieve speckle reduction via non-coherent compounding. Each of the N RF images is formed using X transmit events (X shots). The transmissions can be focused beams, plane waves, or diverging waves. Examples of suitable acquisition types is discussed in Nikolov et al., "Practical Applications of Synthetic Aperture Imaging," 2010 IEEE International Ultrasonics Symposium (UIS), San Diego, Calif., 2010.

Figure 11:
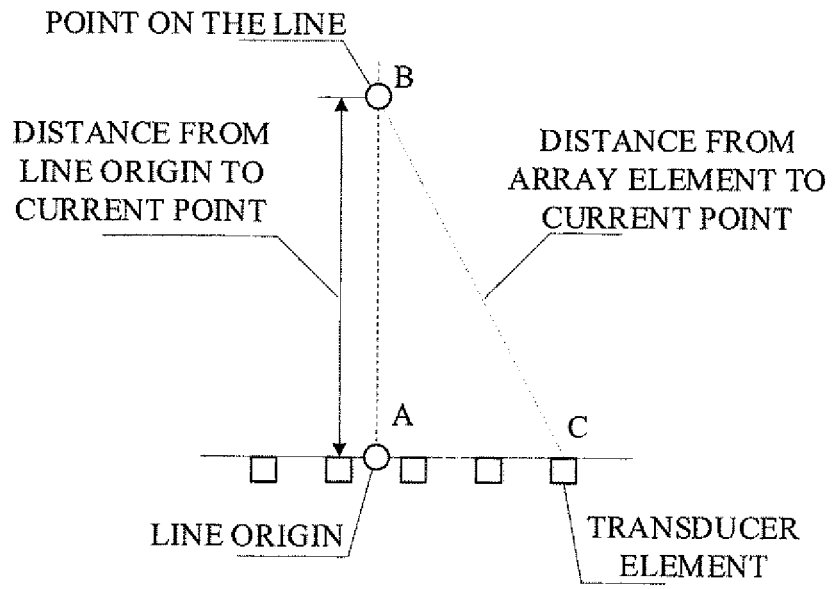
FIG. 11 shows a geometry for a non-steered line.
Figure 12:
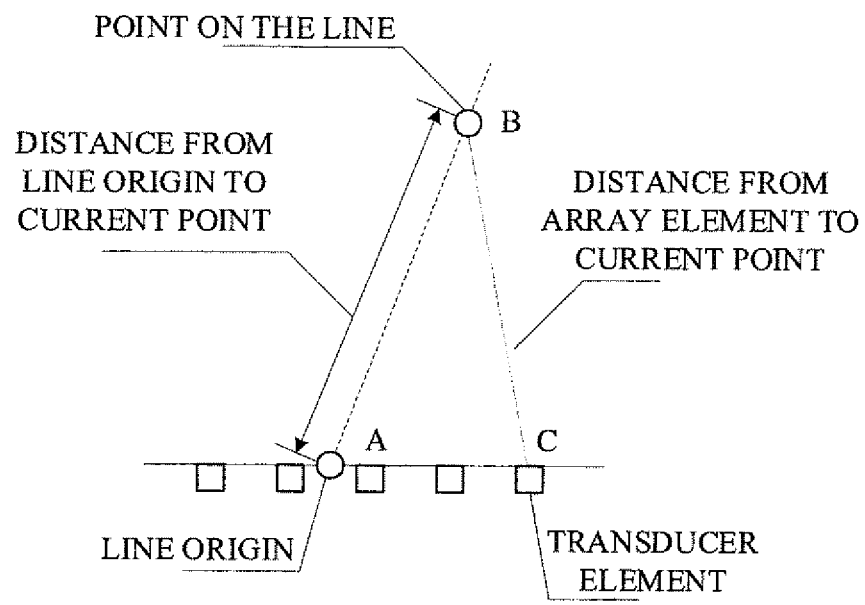
FIG. 12 shows a geometry a steered line.

As briefly discussed above, the dynamic receive focus processor 1002 performs dynamic receive focusing. FIGS. 11 and 12 show a geometry used in the calculation of delays used in dynamic receive focusing. FIG. 11 shows the geometry for a non-steered line, and FIG. 12 shows the geometry for a steered line. The output of the dynamic receive focus processor 1002 are samples $r_l(i)$ along one or multiple lines l, which are produced in this example by using delay-and-sum beamforming.

In one instance, the samples are computed as shown in EQUATION 1:

$$r_l(i) = \sum_{e=0}^{E} a_l(i,e) \cdot g_e(i - f_s \tau_l(i,e)), \; 0 \leq l \leq L-1, \qquad \text{EQUATION 1}$$

where L is a number of lines in one image plane for a single RF image, $g_e(i)$ is a sampled signal received by element with index e, $f_s$ is a sampling frequency, $\tau_l(i, e)$ is a delay for beam b which depends on a sample index along a line i and an element index e, and $a_l(i, e)$ is a weighting coefficient which is a function of the focusing number (distance to focus point divided by aperture width). The delay $\tau$ is equal to a difference in propagation time from a line origin A to a point on a line B, and from a transducer element C to a point on the line B. The delay can be computed as shown in EQUATION 2:

$$\tau = \frac{|AB| - |BC|}{c}, \qquad \text{EQUATION 2}$$

where c is the speed of sound.

Although the dynamic receive focus processor 1002 employs a delay-and-sum beamforming approach in this example, it is to be understood that other approaches are contemplated herein. For example, another suitable approach is adaptive beamforming using coherence factor or based on minimum variance.

The multi-line synthesis processor 1004 combines RF lines formed using different transmissions to produce a new line which has more uniform focusing and higher signal to noise ratio. In one instance, this corresponds to the generation of high resolution images in synthetic aperture focusing, including coherent plane wave compounding. Examples of such are discussed in Lockwood et al., "Real-time {3-D} ultrasound imaging using sparse synthetic aperture beamforming," IEEE Trans. Ultrason. Ferroelec., Freq. Contr., vol. 45, pp. 980-988, 1998, Bae, "Ultrasonic Signal Focusing Method and Apparatus for Ultrasonic Imaging System", U.S. Pat. No. 6,231,511, 2001, Priority Date 10 Nov. 1998, Nikolov et al., "Practical Applications of Synthetic Aperture Imaging," in 2010 IEEE International Ultrasonics Symposium (UIS), 2010, San Diego, Calif., 2010, and Jeong et al., "Beamforming using the synthetic sinc wave for ultrasonic imaging system," in Proc. IEEE Ultrason. Symp., 2001, vol. 2.

In one instance, the multi-line synthesis processor 1004 delays and sums as shown in EQUATION 3:

$$y_l(i) = \sum_{x \in X_l} b_l(i, x) \cdot r_{lx}(i - f_s \cdot \tau_l(i, x)), \quad \text{EQUATION 3}$$

$$0 \le l \le L-1,$$

where $r_{lx}(i)$ is an l-th RF line formed at transmission x, $f_s$ is a sampling frequency and $\tau_l(i,x)$ is a delay that depends on a wavefront created at transmission x relative to the geometry of the formed line at point with index i. The lines $r_{lx}(i)$ are formed using EQUATION 1, where the receive delays have been calculated based on the propagation from the line origin to the reconstructed point and back to the transducer elements. $X_l$ is the set of emissions which create a beam that passes through samples $y_l(i)$.

The parameter $b_l(i,x)$ is a weighting factor for the line l which is a function of sample index i and emission index x. In one instance, $b_l(i,x)$ is computed as shown in EQUATION 4:

$$b_l(i, x) = \begin{cases} 1 & r_{lx}(i - f_s \cdot \tau_l(i, x)) \text{ inside beam} \\ 0 & \text{otherwise} \end{cases} \quad \text{EQUATION 4}$$

Other approaches for computing $b_l(i,x)$ are also contemplated herein. For example, another suitable approach is discussed in Nikolov et al., "Practical Applications of Synthetic Aperture Imaging," in 2010 *IEEE International Ultrasonics Symposium (UIS)*, 2010, San Diego, Calif., 2010.

The multi-line synthesis processor 1004 uses a second set of delays, which takes into account the propagation of the transmit wavefront from the origin of transmission to the reconstructed point.

Figure 13:
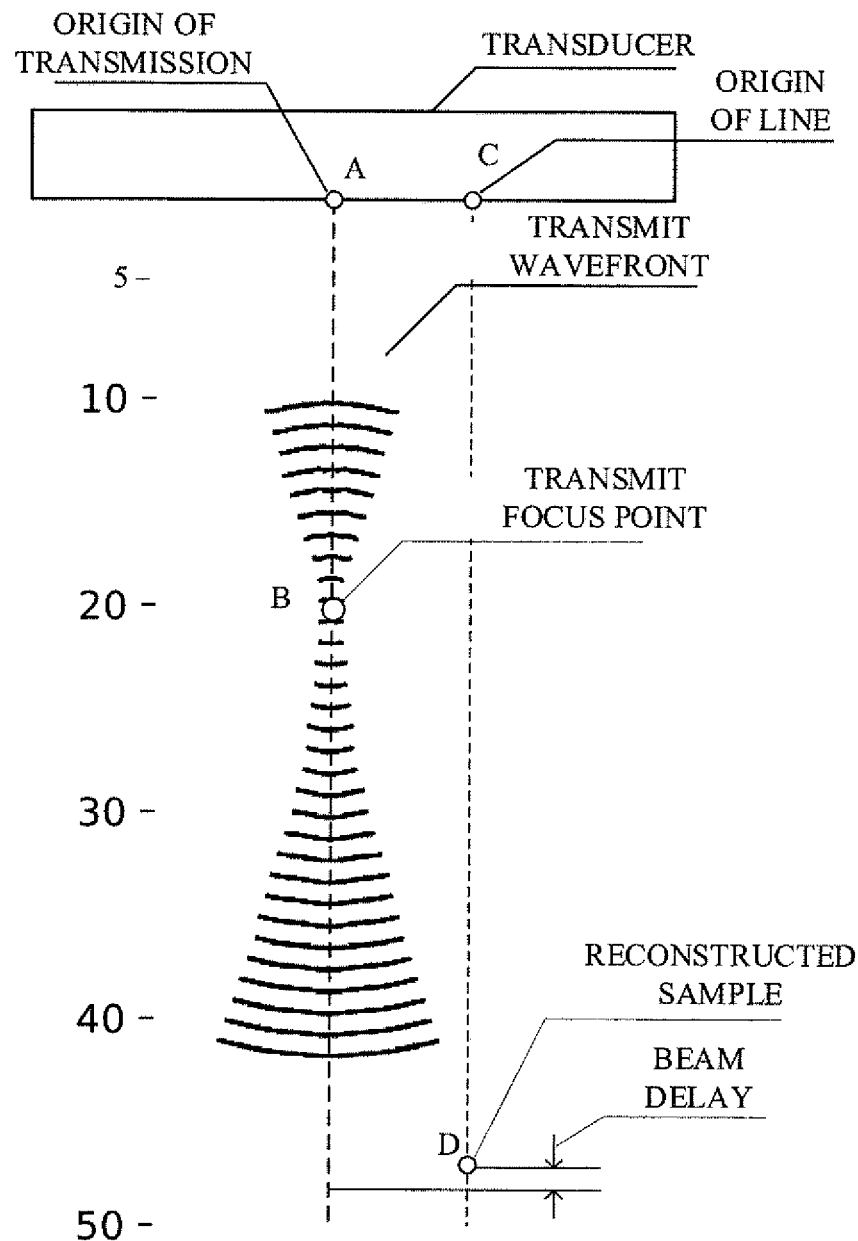
FIG. 13 shows an example wavefront for a focused transmission.

FIG. 13 shows an example wavefront (f-number=3) for a focused transmission. The transmitted beam has an origin A and is focused at the focus point B. The geometric transmit focus B in this example is 20 mm from the transducer surface. The wavefront is shown as a peak of the wavefront at a given time instance. The figure shows the case of forming an RF line that passes through the two points C and D. The beam delay r for the sample at point D is calculated from the difference in propagation times from the origin of transmission A through the focus point B to the reconstructed sample at point D, and the propagation time from the origin of the line C to the reconstructed point D.

A model using the concept of virtual sources is discussed in Bae, "Ultrasonic Signal Focusing Method and Apparatus for Ultrasonic Imaging System", U.S. Pat. No. 6,231,511, 2001, Priority Date 10 Nov. 1998, and Nikolov et al., "Practical Applications of Synthetic Aperture Imaging," in 2010 *IEEE International Ultrasonics Symposium (UIS)*, 2010, San Diego, Calif., 2010. For a point beyond the focus, the delay can be computed as shown in EQUATION 5:

$$\tau = \frac{|AB| + |BD| - |CD|}{c}, \quad \text{EQUATION 5}$$

where c is the speed of sound, and |AB|, |BC| and |CD| are the distances between the respective points.

Another suitable model is discussed in Hansen et al., "Synthetic aperture imaging using a semi-analytic model for the transmit beams," in *Medical Imaging* 2015: *Ultrasonic Imaging and Tomography*, 2015, vol. 1, p. 94190K, and Nikolov et al., "Synthetic aperture imaging using a semi-analytic model for the transmit beams," in 2015 *IEEE International Ultrasonics Symposium (IUS)*, 2015, pp. 1-4. The set of transmissions that contribute to every line is determined from the intensity profile of the transmit beam and is also described in these two references. Delays for diverging beams and plane wave transmissions are discussed in Nikolov et al., "Practical Applications of Synthetic Aperture Imaging," in 2010 *IEEE International Ultrasonics Symposium (UIS)*, 2010, San Diego, Calif., 2010.

Figure 14:
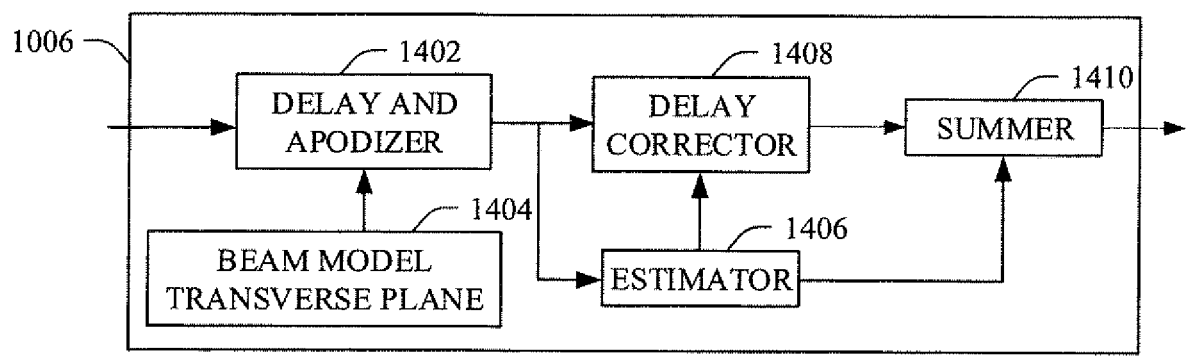
FIG. 14 schematically illustrates an example of the multi-plane synthesis processor.

The multi-plane synthesis processor 1006 synthesizes a volumetric image with higher resolution than that of each individual imaging plane. FIG. 14 schematically illustrates a non-limiting example of the multi-plane synthesis processor 1006.

In this example, a delay and apodizer 1402 delays and weights the signal is using delays and weight coefficients calculated from a model 1404 of the beam in the transverse plane. An estimator 1406 estimates a phase shift (time mismatch) between the signals from the individual planes and produces two values, a delay correction and a weight factor for adaptive summation.

A delay corrector 1408 applies the delay correction to the already delayed signal. In general, the delay correction is a gross-delay correction which compensates for mechanical jitter, jitter in trigger signals, and eventual gross mismatch in the speed of sound. A summer 1410 applies the weight factor on the beam based on a correlation magnitude to prevent degradation of image by adding signals that are not correlated.

Examples of the multi-plane synthesis and for determining the delay correction and the weight factor are described next. The extent (thickness) of the lines from neighboring image planes overlap, and contain echoes generated by the tissue from the overlapping regions. The echoes have different magnitude and phase depending on the position of the scatterers relative to line.

Figure 15:
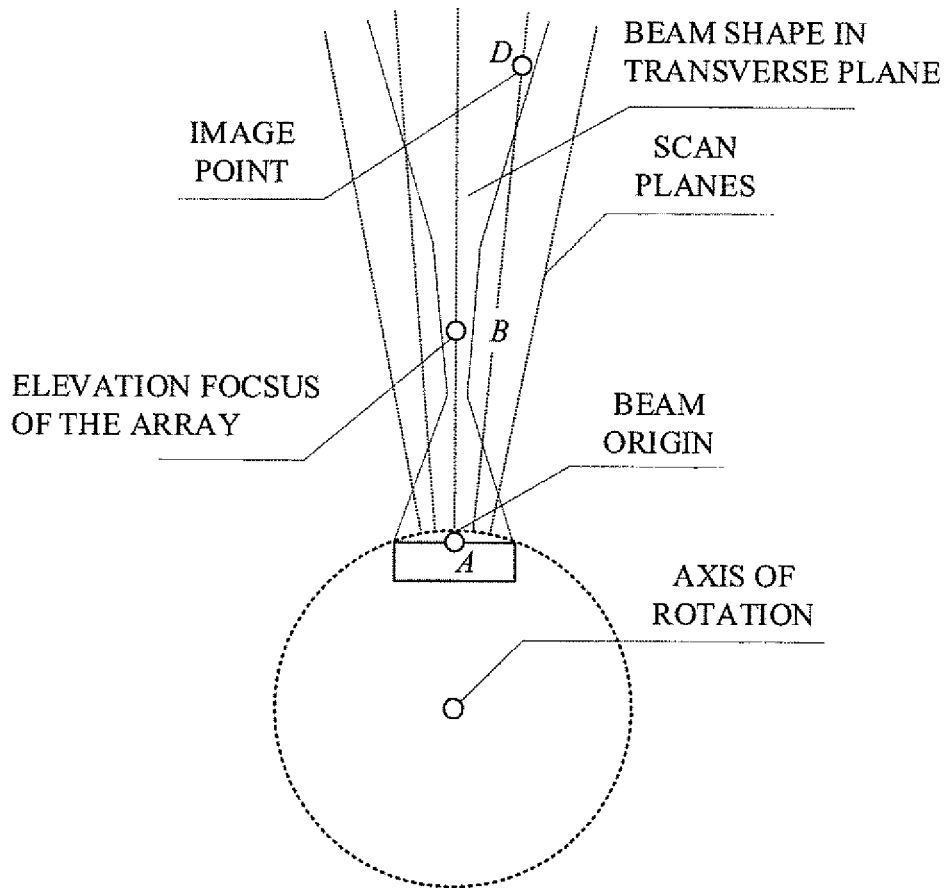
FIG. 15 illustrates the beam shape in the transverse plane.
Figure 16:
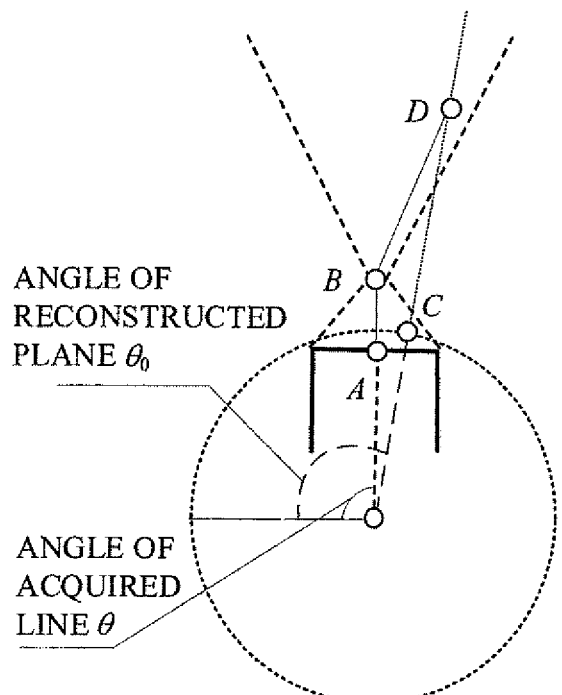
FIG. 16 illustrates the scan geometry the transverse plane.

FIG. 15 illustrates the beam shape in the transverse plane, and FIG. 16 illustrates the scan geometry the transverse plane. The scan planes for the volume are distributed uniformly as a function of rotation angle θ. The shape of the beam in the elevation plane is similar to that of a focused transmission. It is focused by an acoustic lens, and passes through liquid in the transducer shaft, which also affects the wavefront. In the illustrated case, the transducer is focused at a distance |AB| where A is the point at the center of the transducer elements and B is often referred to as elevation focus.

The beam spans many planes (lines), especially close to the surface of the transducer. The lines $v_{l\theta}(i)$ that constitute the final volume are formed by coherently compounding lines $y_{l\theta}(i)$, which lie in the same transverse plane, but different imaging planes scanned at angles θ. In one instance, $v_{l\theta}(i)$ is computed as shown in EQUATION 6:

$$v_{l\theta_0}(i) = \sum_{\theta \in \Theta} c_l(i, \theta) \cdot e(i, \theta) \cdot y_{l\theta}(i - f_s \cdot (\tau_l(i, \theta) + \delta(i, \theta))), \quad \text{EQUATION 6}$$

where i is a sample index along the line defined by the line index (in imaging plane) l and an angle of rotation $\theta_0$, $y_{l\theta}(i)$ are samples of a line with index l acquired at an angle $\theta$, $\Theta$ is the set of planes whose rotation angles $\theta$ are around the plane $\theta_0$, $c_l(i, \theta)$ is a weighting coefficient which is calculated similarly to the coefficients in the multi-line synthesis (EQUATION 4), w(i, $\theta$) are adaptive weights calculated by the estimator 146, $\tau_l(i, \theta)$ is a delay determined from a difference of the two-way propagation time from the origin of the beam A through the focus point B to the point in the image D, and from the origin of the line C to the point D, and $\delta(i, \theta)$ is a correction to delay $\tau_l(i, \theta)$ and is needed to compensate errors in the delays due to mismatch between the assumed position of the plane $\theta$ and the actual angle $\hat{\theta}$.

The mismatch can be caused by acceleration of the transducer and noise due to quantization of time when the trigger signal is propagated through the system. This correction may also minimize errors due to mismatch between the actual speed of sound in the tissue and the speed of sound used in the calculations of the delays. Using the concept of virtual sources, the delay can be calculated as shown in EQUATION 7:

$$\tau_l(i, \theta) = \frac{2}{c}(|AB| \pm |BD| - |CD|). \quad \text{EQUATION 7}$$

If D is between A and B, then the sign in EQUATION 7 is negative (−), otherwise it is positive (+). The factor two (2) in the numerator comes from the 2-way propagation. The virtual source model is not adequate for larger f-numbers (f-number>2). In these case, a semi-analytic beam model can be used. Examples are discussed in Hansen et al., "Synthetic aperture imaging using a semi-analytic model for the transmit beams," in *Medical Imaging* 2015: *Ultrasonic Imaging and Tomography*, 2015, vol. 1, p. 94190K, and Nikolov et al., "Synthetic aperture imaging using a semi-analytic model for the transmit beams," in 2015 *IEEE International Ultrasonics Symposium (IUS)*, 2015, pp. 1-4.

The estimator 1406 determines the correction of delays. For this example of the correction of delays, a sharply focused transducer is considered as the virtual source model.

Figure 17:
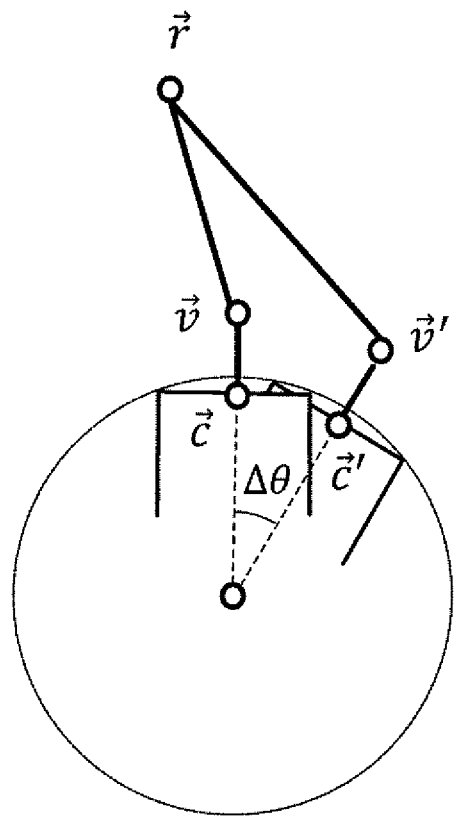
FIG. 17 illustrates the effects of mechanical jitter for a rotational component of motion.

The estimator 1406 determines differences between the calculated time of flights and generates the correction value $\delta_n(i, \theta)$ based thereon. An example of generating the correction value is described in connection with FIG. 17. FIG. 17 illustrates the effects of mechanical jitter for a rotational component of motion. A difference in the angular position of the transducer is $\Delta\theta$ between the expected and the actual angle. For sharply focused transducers, the virtual source model predicts that the propagation of the sound from the transducer surface to a point in the image with coordinates $\vec{r}$ ($\vec{r}$ corresponds to point D from FIGS. 15 and 16) follows the path $\vec{c} \rightarrow \vec{v} \rightarrow \vec{r}$, where $\vec{c}$ are the coordinates of the geometric center of the transducer element in transverse plane and $\vec{v}$ is the (elevation) focus point. $\vec{c}$ are the coordinates of point A in FIGS. 15 and 16, and $\vec{v}$ are the coordinates of point B in FIGS. 15 and 16.

The propagation time from the transducer surface to a point D (FIGS. 15 and 16) and back is defined (subscripts are omitted for conciseness) as shown in EQUATION 8:

$$T(\vec{r}) = \frac{2}{c} \cdot (|\vec{v} - \vec{c}| + |\vec{r} - \vec{v}|), \quad \text{EQUATION 8}$$

where c is the speed of sound, and $|\vec{v} - \vec{c}|$ and $|\vec{r} - \vec{v}|$ are the lengths of the line segments connecting the respective points. The factor two (2) comes from the two-way propagation, like in monostatic radar. The real propagation time is shown in EQUATION 9:

$$T'(\vec{r}) = \frac{2}{c} \cdot (|\vec{v}' - \vec{c}'| + |\vec{r} - \vec{v}'|), \quad \text{EQUATION 9}$$

where $\vec{c}'$ and $\vec{v}'$ are the actual positions of the transducer center and focus points, respectively. The actual propagation time can be expressed as shown in EQUATION 10:

$$T'(\vec{r}) = T(\vec{r}) + \delta_n(\vec{r}), \quad \text{EQUATION 10:}$$

where $\delta_n(\vec{r})$ is the difference in arrival time due to the jitter in mechanical position, which in FIG. 16 is due to difference in angle $\Delta\theta$.

The beamformed complex signal (after DRF and MLS) from a point scatterer can be expressed as shown in EQUATION 11:

$$y(t) = A(t) \cdot e^{(-j2\pi f_0 t)}, \quad \text{EQUATION 11:}$$

where A(t) is an envelope function such as Gaussian, $f_0$ is a carrier frequency, and t is time. y(t) is the beamformed signal after multi-line synthesis from EQUATION 3. The index of the line l, and the angle $\theta$ are omitted for notational simplicity. For the same reason, the index of the sample i is substituted by the actual time t to decrease the number of symbols in the equation. The duration of A(t) is several periods of the carrier signal. This can be approximated with a rectangular window as shown in EQUATION 12:

$$A(t) = \begin{cases} 1, & -T_p/2 < t < T_p/2 \\ 0, & \text{otherwise,} \end{cases} \quad \text{EQUATION 12}$$

where $T_p$ is the duration of the pulse.

After delaying the signals with a delay calculated using the beam model, the signal can be expressed as shown in EQUATION 13:

$$y(\vec{r}) = s(t - T'(\vec{r}) + T(\vec{r})) = s(t - \delta(\vec{r}, \theta)) = A(t - \delta(\vec{r}, \theta))e^{(-j2\pi f_0(t - \delta(\vec{r}, \theta)))}, \quad \text{EQUATION 13:}$$

The signal y( ) whose direction (assumed direction) coincides with the line in the image that is currently beamformed (the line on which the point $\vec{r}$ is located), is used as a reference signal $y_0(\vec{r})$. This signal, for this line, is assumed not to have any jitter (all $\_\delta_0(\vec{r})$ are set to zero). All other signals are aligned to it.

To find the deviation in propagation, the cross correlation between the central signal $y_{\theta_0}(\vec{r})$ (at rotation angle $\theta_0$) and the other signals $y_\theta(\vec{r})$ that are used in the synthetic aperture focusing are calculated at lag 0. The signals are first delayed according to the beam model, and then, their delayed versions are correlated as shown in EQUATION 14:

$$yR_\theta(0, \vec{r}) = \frac{\langle y_{\theta_0}(\vec{r}), y_\theta(\vec{r})\rangle}{\|y_{\theta_0}(\vec{r})\|\|y_\theta(\vec{r})\|} = |R_\theta(0, \vec{r})|e^{(-j2\pi f_0 \delta(\vec{r},\theta))} \quad \text{EQUATION 14}$$

where $y_{\theta_0}$ is a central beam, $y_\theta$ is a beam for which a weight has been calculated, $\langle \cdot, \cdot \rangle$ is an inner product, and $\|\cdot\|$ is a 2-norm. The delay $\delta(\vec{r}, \theta)$ is derived from the angle (phase) of the correlation function $R_\theta(0, \vec{r})$ as shown in EQUATION 15:

$$\delta(\vec{r}, \theta) = \frac{1}{2\pi f_0} \angle(R_\theta(0, \vec{r})). \quad \text{EQUATION 15}$$

This estimation procedure is based on a phase-shift technique, used in color flow imaging, and discussed in Kasai et al., "Real-Time Two-Dimensional Blood Flow Imaging Using an Autocorrelation Technique," IEEE Trans. Son. Ultrason., SU-32(3):458-464, 1985.

An alternative approach is to calculate the cross-correlation $R_\theta(k, \vec{r})$ for a series of lags k and search for the location of the peak of $|R_\theta(0, \vec{r})|$. This the approach is used for combined motion compensation and motion estimation in Nikolov et al., "Velocity estimation using recursive ultrasound imaging and spatially encoded signals," In 2000 IEEE Ultrasonics Symposium, Proceedings, An International Symposium (Cat. No. 00CH37121), volume 2, pages 1473-1477. IEEE, 2000.

The difference in the current context is that the deviations $\delta(\vec{r}, \theta)$ are due to difference in transducer position. This means that $\delta(\vec{r}, \theta)$ is a systematic error for a given set of acquisitions. It is possible to find the deviation in position $\vec{c}' - \vec{c}$, using a least squares fit from the beam model and the estimated deviations $\delta(\theta)$. This procedure makes the estimator robust to deviations due to speckle artifacts. The procedure is further enhanced by estimating the signal to noise ratio (SNR), and using only the portions with high SNR in the least squares fit.

The estimator 1406 determines the adaptive weights. In this example, the adaptive weight $w(i, \theta)$ are computed from the magnitude of the normalized cross-correlation at lag 0 as shown in EQUATION 16:

$$w(i, \theta) = F(|R_\theta(0, \vec{r})|). \quad \text{EQUATION 16:}$$

where $\vec{r}$ are the coordinates of the sample with index i along the reconstructed line $v_{\theta_0}(i)$, and $R_\theta(0, \vec{r})$ is calculated using EQUATION 14. $F(\cdot)$ is a non-linear function. An example of suitable $F(\cdot)$ is given in EQUATION 17:

$$w_n(\vec{r}) = \begin{cases} 1 & |R_n(0, \vec{r})| \geq R_2 \\ \frac{|R_n(0, \vec{r})| - R_1}{R_2 - R_1} & R_1 < |R_n(0, \vec{r})| < R_2 \\ 0 & |R_n(0, \vec{r})| \leq R_1 \end{cases} \quad \text{EQUATION 17}$$

For signals highly correlated signals, $w_n$ is closer to one (1), relative to less corrected signals. The function can also be sigmoid or another empirically determined relation. The calculated values of $w_n(\vec{r})$ are smoothed with a low pass filter or a polynomial fit prior to use in the adaptive sum to avoid discontinuities and/or fluctuations in the image brightness.

Figure 18:
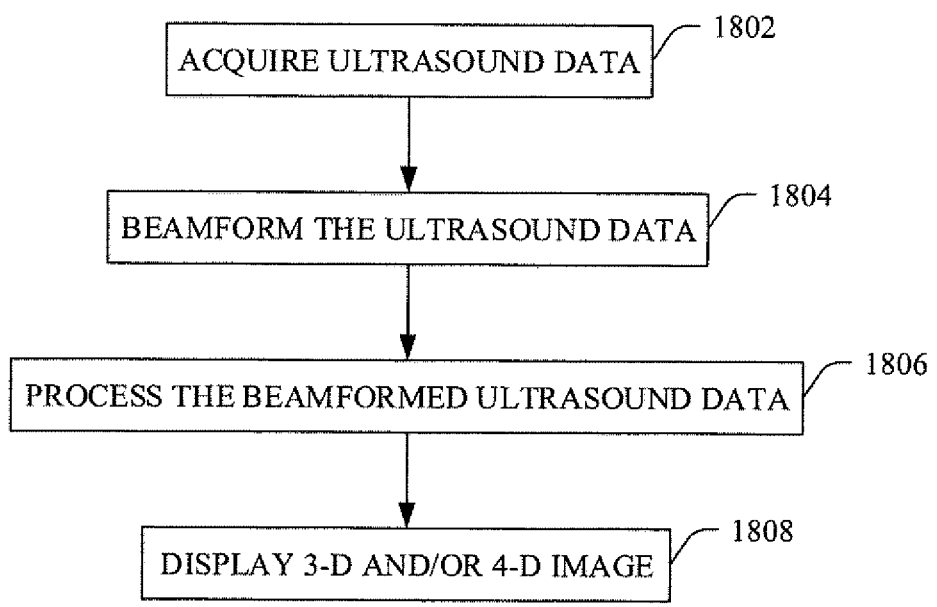
FIG. 18 illustrates a method in accordance with an embodiment herein.

FIG. 18 illustrates a method in accordance with an embodiment herein.

Note that the ordering of the following acts is for explanatory purposes and is not limiting. As such, one or more of the acts can be performed in a different order, including, but not limited to, concurrently. Furthermore, one or more of the acts may be omitted and/or one or more other acts may be added.

At 1802, ultrasound data is acquired as described herein.

At 1804, the ultrasound data is beamformed as described herein.

At 1806, the beamformed ultrasound data is further processed as described herein.

At 1808, the resulting 3-D and/or 4-D image is displayed.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a probe, including:
   an elongate shaft with a long axis;
   a transducer array disposed on the shaft along the long axis and configured to generate signals indicative of received echoes; and
   a motor with a position sensor; and
   a motor controller configured to control the motor to rotate the shaft within a predetermined arc; and
   a console, including:
   a beamformer configured to process the signals from the transducer array and generate at least a volume of data for each sweep of the transducer array along the arc by:
   adding a header to each of the received signals, wherein the header includes an angular position of the transducer array at which a corresponding signal is acquired;
   delaying and summing the signals to produce a set of lines in the imaging plane for every transmission;
   delaying and weighting lines of the set of lines that have a same origin and direction, but are acquired with different transmissions; and
   delaying and weighting lines of the set of lines acquired from different imaging planes, but have a same origin and direction relative to the transducer array at a given angular position;
   wherein the delays and weights are calculated in accordance to a shape of the beam in a transverse plane;
   wherein the generated volume of data includes compounding the set of lines that lie in the same transverse plane but different imaging plane scanned at the given angular position;
   and a display configured to display the volume of data.

2. The ultrasound imaging system of claim 1, wherein the beamformer delays and weights the lines from the different imaging planes with coefficients based on a plane transverse to the imaging planes.

3. The ultrasound imaging system of claim 1, wherein the beamformer further estimates a phase shift time mismatch between the signals from the different imaging planes to produce two values, a delay correction and a weight factor for adaptive summation.

4. The ultrasound imaging system of claim 3, wherein the beamformer further applies the delay correction to the delayed signal.

5. The ultrasound imaging system of claim 1, wherein the console is configured to transmit rotation control parameters to the probe, which utilizes the rotation control parameters to control the rotation of the transducer array.

6. The ultrasound imaging system of claim 5, wherein the rotation control parameters include a parameter from a group consisting of: start angular position; stop angular position; speed of rotation; direction of rotation; and number of synchronization pulses to generate between the start and stop positions.

7. The ultrasound imaging system of claim 1, wherein the probe is configured to transmit an angular position of the transducer array, a rotation direction of the transducer array, and a trigger to the console.

8. The ultrasound imaging system of claim 4, further comprising:
a vector processor configured to perform bandpass filtration, gain adjustment, envelope detection, and decimation on the multi-plane synthesized data, producing vector processed data.

9. The ultrasound imaging system of claim 8, further comprising:
a compounder configured to perform non-coherent compounding on the vector processed data, producing compounded data.

10. The ultrasound imaging system of claim 9, further comprising:
an image processor configured to perform filtration and enhancement of the compounded data, producing display data.

11. The ultrasound imaging system of claim 10, wherein the display is configured to display the display data.

12. The ultrasound imaging system of claim 11, wherein the display data is 3-D data.

13. The ultrasound imaging system of claim 11, wherein the display data is 4-D data.

14. A method, comprising:
receiving signals from an ultrasound probe, which includes an elongate shaft with a long axis, a one-dimensional transducer array disposed the shaft along the long axis and configured to generate the signals indicative of received echoes, and a motor with a position sensor and a motor controller configured to control the motor to rotate the shaft within a predetermined arc;
beamforming the signals to generate at least a volume of data for each sweep of the transducer array along the arc by:
adding a header to each of the received signals, wherein the header includes an angular position of the transducer array at which a corresponding signal is acquired;
delaying and summing the signals to produce a set of lines in the imaging plane for every transmission;
delaying and weighting lines of the set of lines that have a same origin and direction, but are acquired with different transmissions;
and delaying and weighting lines of the set of lines acquired from different imaging planes, but have a same origin and direction relative to the transducer array at a given angular position;
wherein the delays and weights are calculated in accordance to a shape of the beam in a transverse plane;
wherein the generated volume of data includes compounding the set of lines that lie in the same transverse plane but different imaging plane scanned at the given angular position;
and displaying the volume of data.

15. The method of claim 14, further comprising:
performing B-mode processing on the at least the volume of data;
compounding the B-mode processed at least the volume of data;
visually enhancing the compounded B-mode processed at least the volume of data; and
presenting the visually enhanced compounded B-mode processed at least the volume of data.

16. A non-transitory computer readable medium encoded with computer executable instructions which when executed by a processor causes the processor to:
receive signals from an ultrasound, which includes an elongate shaft with a long axis, a one-dimensional transducer array disposed the shaft along the long axis and configured to generate the signals indicative of received echoes, and a motor with a position sensor and a motor controller configured to control the motor to rotate the shaft within a predetermined arc;
beamform the signals to generate at least a high-resolution and high-contrast volume of data for each sweep of the transducer array along the arc by:
adding a header to each of the received signals, wherein the header includes an angular position of the transducer array at which a corresponding signal is acquired;
delaying and summing the signals to produce a set of lines in the imaging plane for every transmission;
delaying and weighting lines of the set of lines that have a same origin and direction, but are acquired with different transmissions;
and delaying and weighting lines of the set of lines acquired from different imaging planes, but have a same origin and direction relative to the transducer array at a given angular position;
wherein the delays and weights are calculated in accordance to a shape of the beam in a transverse plane;
wherein the generated volume of data includes compounding the set of lines that lie in the same transverse plane but different imaging plane scanned at the given angular position;
and visually present the high-resolution and high-contrast volume of data.

17. The computer readable medium of claim 16, wherein the instructions further cause the processor to: process, and visually enhance the beamformed data; and display the processed, compounded, and visually enhanced data.

18. The ultrasound imaging system of claim 4, wherein the delay correction is a gross-delay correction which compensates for mechanical jitter, jitter in trigger signals, and gross mismatch in the speed of sound.

19. The ultrasound imaging system of claim 4, wherein the beamformer further applies the weight factor based on a correlation magnitude.

20. The ultrasound imaging system of claim 4, wherein the beamformer further applies the weight factor by adding signals that are not correlated.

21. The ultrasound imaging system of claim 3, wherein the beamformer determines the delay correction based on a cross-correlation between a central signal and non-central signals.

22. The ultrasound imaging system of claim 21, wherein the beamformer determines the cross-correlation for a series of lags by searching for a location of a peak.

23. The ultrasound imaging system of claim 3, wherein the beamformer determines the weight factor from a magnitude of a normalized cross-correlation at lag 0.

* * * * *